United States Patent
Blaustein et al.

(10) Patent No.: US 6,836,917 B2
(45) Date of Patent: Jan. 4, 2005

(54) REPLACEABLE HEAD ELECTRIC TOOTHBRUSH AND CONNECTION STRUCTURE THEREFOR

(75) Inventors: Lawrence A. Blaustein, Moreland Hills, OH (US); John Osher, Moreland Hills, OH (US); Douglas A. Gall, Westlake, OH (US); John G. Chan, Beijing (CN); K. S. Chan, Hong Kong (HK); Ping Wang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 324 days.

(21) Appl. No.: 09/850,662

(22) Filed: May 7, 2001

(65) Prior Publication Data

US 2002/0162180 A1 Nov. 7, 2002

(51) Int. Cl.[7] ............................ A61C 17/34; A46B 13/02
(52) U.S. Cl. ............................................ 15/22.1; 15/28
(58) Field of Search .............................. 15/23, 28, 22.1, 15/24, 29, 22.2; 403/380, 313, 314, 326, 374, 377

(56) References Cited

U.S. PATENT DOCUMENTS

| | | |
|---|---|---|
| 303,474 A | 8/1884 | Webb |
| 793,587 A | 6/1905 | Johnson |
| 796,084 A | 8/1905 | Orr |
| 1,033,187 A | 7/1912 | Metzger |
| 1,593,763 A | 7/1926 | Henderson |
| 1,712,579 A | 5/1929 | Nichols |
| 1,945,616 A | 2/1934 | Mastrud |
| 1,947,324 A | 2/1934 | Zerbee |
| 2,044,863 A | 6/1936 | Sticht |
| 2,196,667 A | 4/1940 | Moseley |

(List continued on next page.)

FOREIGN PATENT DOCUMENTS

| | | | |
|---|---|---|---|
| AU | 47934/93 | 2/1994 | |
| CA | 2004600 | 6/1990 | |
| CA | 1288555 | 9/1991 | |
| CA | 2071880 | 2/1995 | |
| CA | 2135909 | 7/1998 | |
| CA | 2141569 | 2/2000 | |
| CN | 2200419 | 6/1995 | |
| CN | 2274947 | 1/1998 | |
| DE | 1457372 | 4/1969 | |
| DE | 4376046 | 10/1976 | |
| DE | G8426426.8 | 3/1985 | |
| DE | 3544-256 A | 6/1987 | |
| DE | 4003305 A1 | 8/1991 | ................ 15/22.2 |
| DE | 41 39 788 A1 | 6/1993 | |
| DE | G9313167.4 | 12/1993 | |
| DE | 4243221 A1 | 6/1994 | |
| DE | 4313970 A1 | 11/1994 | |
| DE | 296 00236 U1 | 4/1996 | |
| DE | 19508932 A1 | 9/1996 | |
| DE | 4318976 C2 | 12/1996 | |
| DE | 19520303 | 12/1996 | |
| DE | 296 18 755 U1 | 1/1997 | |
| DE | 297 01 302 U1 | 8/1997 | |
| DE | 19701964 A1 | 7/1998 | |
| DE | 298 21 331 U1 | 2/1999 | |
| DE | 298 09 977 U1 | 4/1999 | |

(List continued on next page.)

Primary Examiner—Gary K. Graham
(74) Attorney, Agent, or Firm—James C. Vago (57) ABSTRACT

An electric toothbrush comprising an elongated body portion and a head including a static portion and a moving portion, a handle, and an angled shaft between the head and the handle. The portion of the toothbrush containing the head is detachably connected to the portion of the toothbrush containing the handle. A shaft within the head is selectively connectable to a mating shaft within the handle by a cooperating notch and peg assembly biased into a locking position by a spring member disposed to bias the head shaft into the desired position.

22 Claims, 8 Drawing Sheets

U.S. PATENT DOCUMENTS

| | | | |
|---|---|---|---|
| 2,215,031 A | 9/1940 | Elmore | |
| 2,250,975 A | 7/1941 | Sussman | |
| 2,299,357 A | 10/1942 | Strunk et al. | |
| 2,448,614 A | 9/1948 | Mirus | |
| 2,476,154 A | 7/1949 | Lohs | |
| 2,516,195 A | 7/1950 | Finton | |
| 2,558,332 A | 6/1951 | Artale | |
| 2,598,275 A | 5/1952 | Lakin | |
| 3,043,614 A | 7/1962 | Eichmann | |
| 3,072,938 A | 1/1963 | Phaneuf | |
| 3,142,852 A | 8/1964 | Phaneuf et al. | |
| 3,152,810 A | 10/1964 | Brinkman | |
| 3,158,884 A * | 12/1964 | Monti-Buzzetti | 15/23 |
| 3,160,902 A | 12/1964 | Aymar | |
| 3,178,754 A | 4/1965 | Cleverdon | |
| 3,181,189 A | 5/1965 | Leyden | |
| 3,195,537 A | 7/1965 | Blasi | |
| 3,240,077 A | 3/1966 | Smith | |
| 3,242,516 A | 3/1966 | Cantor | |
| 3,379,906 A | 4/1968 | Spohr | |
| 3,400,417 A | 9/1968 | Moret | 15/22.2 |
| 3,533,119 A | 10/1970 | Dokos | |
| 3,535,726 A | 10/1970 | Sawyer | |
| 3,577,579 A | 5/1971 | Duve et al. | |
| 3,588,936 A | 6/1971 | Duve | |
| 3,595,126 A | 7/1971 | Norton | |
| 3,802,420 A | 4/1974 | Moffat et al. | |
| 3,829,922 A | 8/1974 | Koblanski | |
| 3,851,984 A | 12/1974 | Crippa | |
| 3,978,852 A | 9/1976 | Annoni | |
| 4,123,845 A | 11/1978 | Fattaleh | |
| 4,181,997 A | 1/1980 | O'Rourke | 15/24 |
| 4,203,431 A | 5/1980 | Abura et al. | 128/39 |
| 4,274,173 A | 6/1981 | Cohen | 15/28 |
| 4,281,987 A | 8/1981 | Kleesattel | 433/103 |
| 4,365,376 A | 12/1982 | Oda et al. | |
| 4,374,354 A | 2/1983 | Petrovic et al. | |
| 4,397,055 A | 8/1983 | Cuchiara | |
| 4,450,599 A | 5/1984 | Scheller et al. | |
| 4,665,921 A | 5/1987 | Teranishi et al. | |
| 4,780,924 A | 11/1988 | Hansen et al. | |
| 4,827,550 A | 5/1989 | Graham et al. | |
| 4,827,552 A | 5/1989 | Bojar et al. | |
| 4,845,795 A | 7/1989 | Crawford et al. | 15/22.1 |
| 4,880,382 A | 11/1989 | Moret et al. | |
| 4,989,287 A | 2/1991 | Scherer | |
| 4,991,249 A | 2/1991 | Suroff | 15/22.1 |
| 5,000,684 A | 3/1991 | Odrich | 15/22.1 |
| 5,033,150 A | 7/1991 | Gross et al. | |
| 5,054,149 A | 10/1991 | Si-Hoe et al. | |
| 5,068,939 A | 12/1991 | Holland | 15/22.1 |
| 5,070,567 A | 12/1991 | Holland | 15/28 |
| 5,071,348 A | 12/1991 | Woog | |
| 5,072,482 A | 12/1991 | Bojar et al. | 15/180 |
| 5,077,855 A | 1/1992 | Ambasz | 15/22.2 |
| 5,088,145 A | 2/1992 | Whitefield | 15/22.2 |
| 5,099,536 A * | 3/1992 | Hirabayashi | 15/28 |
| 5,142,723 A | 9/1992 | Lustig et al. | |
| 5,148,567 A | 9/1992 | Daub | |
| 5,170,525 A | 12/1992 | Cafaro | |
| 5,177,826 A | 1/1993 | Vrignaud | 15/22.1 |
| 5,186,627 A | 2/1993 | Amit et al. | 15/22.1 |
| 5,213,434 A | 5/1993 | Hahn | |
| 5,226,206 A | 7/1993 | Davidovitz et al. | 15/22.1 |
| 5,253,382 A | 10/1993 | Beny | |
| 5,259,083 A | 11/1993 | Stansbury, Jr. | |
| 5,274,870 A | 1/1994 | Stollman | 15/22.1 |
| 5,276,932 A | 1/1994 | Byrd | |
| 5,283,921 A | 2/1994 | Ng | |
| 5,289,604 A | 3/1994 | Kressner | 15/22.1 |
| 5,311,632 A | 5/1994 | Center | |
| 5,311,633 A | 5/1994 | Herzog et al. | |
| 5,341,534 A | 8/1994 | Serbinski et al. | 15/22.1 |
| 5,353,460 A | 10/1994 | Bauman | |
| 5,359,747 A | 11/1994 | Amakasu | |
| 5,365,627 A | 11/1994 | Jousson et al. | |
| 5,378,153 A | 1/1995 | Giuliani et al. | 15/22.1 |
| 5,381,576 A | 1/1995 | Hwang | |
| 5,383,242 A | 1/1995 | Bigler et al. | |
| 5,399,089 A | 3/1995 | Eichman et al. | |
| 5,404,608 A | 4/1995 | Hommann | |
| 5,416,942 A | 5/1995 | Baldacci et al. | |
| 5,421,726 A | 6/1995 | Okada | |
| 5,435,034 A | 7/1995 | Bigler et al. | |
| 5,442,827 A | 8/1995 | Hommann | |
| 5,448,792 A | 9/1995 | Wiedemann et al. | |
| 5,461,744 A | 10/1995 | Merbach | |
| 5,465,444 A | 11/1995 | Bigler et al. | |
| 5,467,494 A | 11/1995 | Müller et al. | |
| 5,467,495 A | 11/1995 | Boland et al. | |
| 5,504,959 A | 4/1996 | Yukawa et al. | |
| 5,504,960 A | 4/1996 | Hommann | |
| 5,504,961 A | 4/1996 | Yang | |
| 5,524,312 A | 6/1996 | Tan et al. | |
| 5,561,881 A | 10/1996 | Klinger et al. | |
| 5,592,599 A | 1/1997 | Lindholm | |
| 5,613,259 A | 3/1997 | Craft et al. | |
| 5,617,601 A | 4/1997 | McDougall | |
| 5,617,603 A | 4/1997 | Mei | |
| 5,727,273 A | 3/1998 | Pai | |
| 5,732,432 A | 3/1998 | Hui | |
| 5,732,433 A | 3/1998 | Göcking et al. | 15/22.1 |
| 5,774,921 A | 7/1998 | Harrison et al. | |
| 5,822,821 A | 10/1998 | Sham | |
| RE35,941 E | 11/1998 | Stansbury, Jr. | |
| 5,836,030 A | 11/1998 | Hazeu et al. | |
| 5,842,244 A | 12/1998 | Hilfinger et al. | |
| 5,842,245 A | 12/1998 | Pai | |
| 5,862,558 A | 1/1999 | Hilfinger et al. | |
| 5,862,559 A | 1/1999 | Hunter | |
| 5,867,856 A | 2/1999 | Herzog | |
| 5,875,510 A | 3/1999 | Lamond et al. | |
| 5,974,613 A | 11/1999 | Herzog | |
| 5,974,615 A | 11/1999 | Schwarz-Hartmann et al. | |
| 5,987,681 A | 11/1999 | Hahn et al. | |
| 6,015,328 A | 1/2000 | Glaser | |
| 6,047,429 A | 4/2000 | Wu | |
| 6,058,541 A | 5/2000 | Masterman et al. | |
| 6,094,769 A | 8/2000 | Driesen et al. | |
| 6,138,310 A | 10/2000 | Porper et al. | |
| 6,141,815 A | 11/2000 | Harrison et al. | |
| 6,195,828 B1 | 3/2001 | Fritsch | |
| 6,220,772 B1 | 4/2001 | Taylor | |
| 6,226,068 B1 | 5/2001 | Arcykiewicz et al. | |
| 6,237,178 B1 | 5/2001 | Krammer et al. | |
| 6,308,359 B2 | 10/2001 | Fritsch et al. | |
| 6,367,108 B1 | 4/2002 | Fritsch et al. | 15/28 |
| 6,381,795 B1 * | 5/2002 | Hofmann et al. | 15/28 |
| 2002/0162180 A1 | 11/2002 | Blaustein et al. | |
| 2004/0016067 A1 | 1/2004 | Kraemer | |

FOREIGN PATENT DOCUMENTS

| | | |
|---|---|---|
| EP | 0 190-380 A1 | 8/1986 |
| EP | 0 208 401 A2 | 1/1987 |
| EP | 0 254 397 | 1/1988 |
| EP | 0 435329 | 7/1991 |
| EP | 0 357863 | 7/1992 |
| EP | 537465 A2 | 4/1993 |
| EP | 0 547628 | 6/1993 |
| EP | 0 500537 | 11/1994 |
| EP | 0 651978 | 5/1995 |

| | | | | | | |
|---|---|---|---|---|---|---|
| EP | 0 500536 | 10/1995 | | JP | 08299372 | 11/1996 |
| EP | 0865771 | 9/1998 | | JP | 9-019445 | 1/1997 |
| EP | 0 977521 | 2/2000 | | JP | 10023928 | 1/1998 |
| EP | 1 053 721 A1 | 11/2000 | | JP | 10052447 | 2/1998 |
| EP | 1 256327 | 11/2002 | | JP | 1032248 | 12/1998 |
| FR | 1053275 | 2/1954 | | JP | 11-235234 | 8/1999 |
| FR | 1357570 | 4/1964 | | JP | 11-253232 | 9/1999 |
| FR | 1414679 | 9/1965 | | KR | 1994-0013418 | 7/1994 |
| FR | 2368854 A | 5/1978 | | TW | 127530 | 11/1976 |
| FR | 2739763 | 4/1997 | | TW | 179242 | 1/1980 |
| FR | 2770768 | 5/1999 | | TW | 230339 | 4/1983 |
| GB | 452961 | 9/1936 | | TW | 249332 | 6/1983 |
| GB | 477799 | 1/1938 | .................... 15/28 | TW | 311444 | 12/1985 |
| GB | 0500517 | 2/1939 | | TW | 135303 | 6/1990 |
| GB | 914844 | 1/1963 | | TW | 256049 | 1/1993 |
| GB | 1098893 | 6/1966 | | TW | 406557 | 5/1998 |
| GB | 1240438 | 7/1971 | | TW | 338313 | 8/1998 |
| GB | 1293876 | 10/1972 | | WO | WO 83/03956 | 11/1983 |
| GB | 1583558 | 1/1981 | | WO | WO 91/07117 | 5/1991 |
| GB | 369600 | 3/1982 | | WO | WO 91/13570 | 9/1991 |
| GB | 2 225 712 A | 6/1990 | | WO | WO 92/13499 | 8/1992 |
| GB | 2 228 861 A | 9/1990 | | WO | WO 93/09729 | 5/1993 |
| GB | 2 290 224 A | 12/1995 | | WO | WO 93/10721 | 6/1993 |
| JP | U4-133733 | 12/1982 | | WO | WO93/10721 | 6/1993 |
| JP | 60-112926 | 7/1985 | | WO | WO 94/03124 | 2/1994 |
| JP | 63-54324 | 4/1988 | | WO | WO 94/21193 | 9/1994 |
| JP | 405095816 A | 4/1993 | | WO | 97/14329 | 4/1997 |
| JP | 5-48723 | 6/1993 | | WO | WO 97/28757 | 8/1997 |
| JP | 5-146314 | 6/1993 | | WO | 97/43924 | 11/1997 |
| JP | 05207914 | 8/1993 | | WO | 98/01055 | 1/1998 |
| JP | 405199917 A | 8/1993 | | WO | 98/12947 | 4/1998 |
| JP | 05269023 | 10/1993 | | WO | WO 98/23223 | 6/1998 |
| JP | 5-269024 | 10/1993 | | WO | WO 98/47444 | 10/1998 |
| JP | 6-41538 | 6/1994 | | WO | WO 99/20202 | 4/1999 |
| JP | 406245820 A | 9/1994 | | WO | WO 99/23975 | 5/1999 |
| JP | 7-148020 | 6/1995 | | WO | WO 99/56660 | 11/1999 |
| JP | 07255530 | 10/1995 | | WO | WO 99/65359 | 12/1999 |
| JP | 8-103330 | 4/1996 | | WO | 00/15076 | 3/2000 |
| JP | 8-103331 | 4/1996 | | WO | WO 00/76420 | 12/2000 |
| JP | 08224259 | 9/1996 | | | | |
| JP | 8-299372 | 11/1996 | | * cited by examiner | | |

REPLACEABLE HEAD ELECTRIC TOOTHBRUSH AND CONNECTION STRUCTURE THEREFOR

BACKGROUND OF THE INVENTION

The present invention relates generally to electric toothbrushes. More particularly, it relates to an improved powered toothbrush with a replaceable head.

The benefits of brushing one's teeth using motorized toothbrushes are well known, and motorized movement in toothbrushes has been the subject of much recent innovation and design activity. Also, the commercial market has seen the introduction, over the last several years, of many different types of motorized toothbrushes. However, an examination of the available technology shows a tendency toward increasingly complex, expensive, and non-commercially feasible methods of achieving motorized motions in the bristles and heads of toothbrushes to aid in more effectively cleaning one's teeth.

The commercial marketplace has become divided into two price markets. On the higher priced end are some of these more complex motorized toothbrushes that provide various motions to the bristles and brush head. The lower end of the market has become the province of very simple motorized toothbrushes that only vibrate through the use of an offset weight attached to the motor shaft, and which provide very little true additional cleaning benefit with their use, since no vigorous motion is transmitted to the cleaning surface of the brush. The vibrations are also very uncomfortable to the hand and act as a disincentive to brush one's teeth for an adequate time.

Numerous electric toothbrushes have been developed over the years. Some known devices are shown in U.S. Pat. Nos. 5,070,567; 5,186,627; 5,274,870; 5,341,534; 5,378,153; and 5,732,433. The intention of the present invention is to provide a low cost, effective, ergonomically correct, motorized toothbrush which has an easily replaceable brush head. Thus, the user can re-use the toothbrush simply by replacing the brush head after the brush head wears out, or several users can use the same handle with several different toothbrush heads.

Various connection structures for linking the brush head to the motor have been suggested, all with varying degrees of success. Any such structure needs to provide a reliable communication of motorized movement to the brush head from the motor, and yet be easily and repeatably attachable and removable, without debilitating the connection integrity over time. Those prior art structures requiring flexible plastic or "living hinge" components of the shaft assembly that are suspect in this regard due to their normal weakening from repeated flexing, wear or age. The subject invention seeks to provide a linking structure that minimizes these prior art problems by providing a connection assembly that provides a reliable and secure connection without having to repeatably flex system components to an undesirable extent, and where the drive shaft is biased from a side disposed spring operating on the shaft instead of comprising a part of the shaft.

Accordingly it has been considered desirable to develop a new and improved electric toothbrush which would overcome the foregoing difficulties and others while providing better and more advantageous overall results.

SUMMARY OF THE INVENTION

The present invention relates to an electric toothbrush. More specifically, the electric toothbrush has a replaceable brush head and is used in personal hygiene to clean one's teeth and gums using a motorized movement.

According to one embodiment of the present invention, the electric toothbrush includes an elongated body portion, a brush head attached to a first end of the elongated body portion, a handle attached to a second end of the elongated body portion, and an angled shaft between the brush head and the handle. The elongated body portion is comprised of a first member and a second member. The first member is detachably connected to the second member so that the first member that contains the brush head can be thrown away and easily replaced after the brush head wears out.

The brush head includes a longitudinal axis, a moving portion and a static portion. The moving portion rotates, oscillates or reciprocates about an axis normal to the longitudinal axis of the brush head and is incorporated into the larger brush head. The brush head also includes static bristles located adjacent or about the moving portion. The stiff bristles of the moving portion are slightly recessed in height from the static bristles. This particular arrangement allows for the moving portion to include stiff bristles which will aid in the deep cleaning and plaque removal process, while the stationary bristles would typically consist of a softer bristle, so as not to damage the gums.

The brush head has a more traditional larger brush head shape which permits the user to brush his teeth in the typical manner of an up and down fashion, while a motorized moving portion of the brush head cleans more effectively. The design of the brush head allows for inexpensive manufacture and brings effective motorized toothbrushes within the financial reach of a larger portion of the population.

The elongated body portion includes a hollow portion. The toothbrush is further comprised of a motor within the hollow portion of the elongated body portion. The motor is operably connected to the moving portion of the brush head for moving the stiff bristles on the head. The motor has a longitudinal axis which is coaxial with a longitudinal axis of the elongated body portion.

The hollow portion further includes a simplified gear assembly. The gear assembly may comprise any one of several embodiments. In one embodiment, the gear assembly includes a crown gear and a gear linkage. The motor is operatively connected to the crown gear. The gear assembly delivers sufficient torque, speed, and battery longevity. The linkage permits the gear assembly to be offset with respect to a longitudinal axis of the elongated body portion and placed at the desired angle so that the shaft itself can still be straight, thus losing no power or torque through the added friction of a flexible shaft.

The shaft is comprised of a first portion and a second portion. The first and second portions of the shaft are detachably connected to each other. The first portion is operatively attached at one end to the moving portion of the brush head and detachably connected at the other end to the second portion of the shaft. The second portion of the shaft is detachably connected to the first portion of the shaft at one end and operatively connected to the gear assembly at the other end.

In accordance with the present invention, a gearing and shaft assembly operatively connects the moving bristles with the motor. The first and second detachable shafts include a notch and tab connection arrangement at opposed end portions so that the second shaft includes a tab sized for reception in the notch cut in the first shaft. The shaft associated with the moving bristles is biased for selective angular movement within the brushhead towards the first shaft by a spring member so that when the notch and tab are properly aligned, a locking engagement between the two shafts is realized. The desired selected alignment of the head and handle for the locking engagement is facilitated by a guide slot and mating projection assembly within the sidewalls of the head and handle so that when the head is attached to the handle, cooperative reception between the mating projection and the slot aligns the head and handle in the predetermined attached position.

In accordance with a more limited aspect of the present invention, the head includes an inner wall forming an aperture loosely spaced about the head shaft for accommodating the selective angular movement of the shaft during disattachment and attachment of the head onto the handle. An o-ring on the shaft provides a bumper guard against the wall from the reciprocating movement of the head shaft. The spring member is disposed adjacent the apertured wall and in between a wall of the head and the head shaft. Deflection of the head shaft during the locking engagement of the notch and tab assembly is supported by the spring member which will continue to urge the head shaft into the position of locking engagement. Locking engagement is accomplished in accordance with a relative rotational disposition of the head relative to the handle effected by a press-and-twist operator action.

The spring member may comprise any of several substantially equivalent embodiments such as a helical spring, flat spring, or integrally molded, sidewall plastic prongs, or the like.

The electric toothbrush further includes a battery located within the hollow portion of the elongated body portion. A slidable, snap-on cover is depressed then released from the end of the handle and opens to expose the hollow portion. The battery is then inserted and then the cover is slid into position and snapped into place.

Advantages and benefits of the invention will become apparent to those skilled in the art upon a reading and understanding of the following detailed description.

BRIEF DESCRIPTION OF THE DRAWINGS

The invention may take physical form in certain parts and arrangements of parts, embodiments of which will be described in detail in this specification and illustrated in the accompanying drawings which form a part hereof, and wherein.

DETAILED DESCRIPTION OF AN EMBODIMENT

Figure 1:
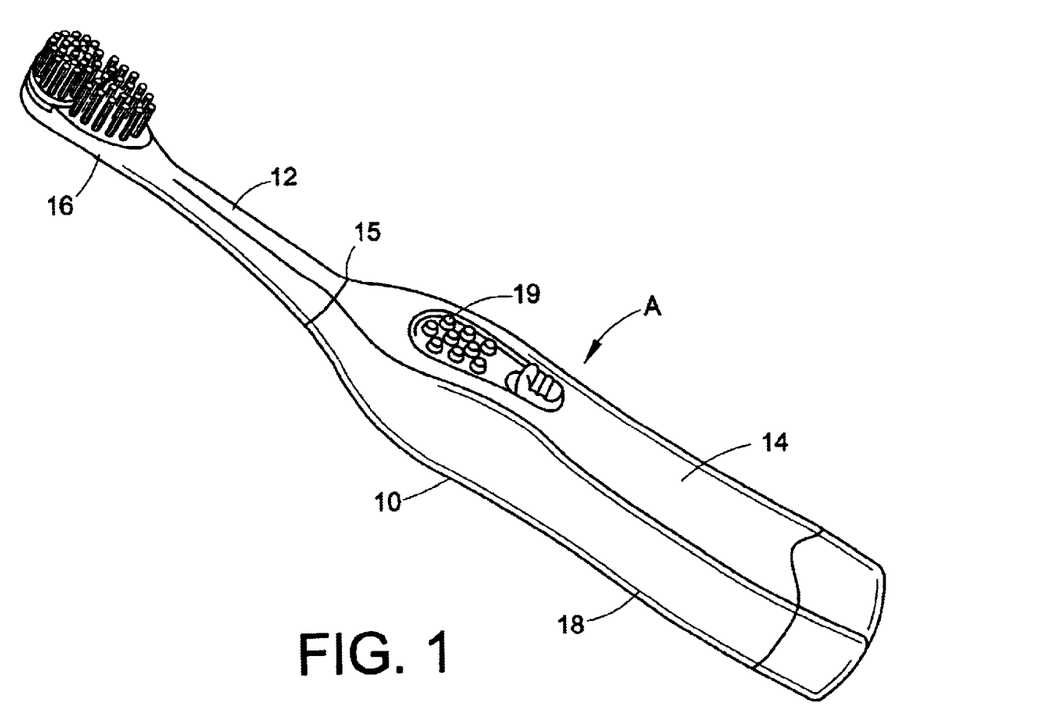
FIG. 1 is a perspective view of the electric toothbrush in accordance with one embodiment of the present invention.

Referring now to the drawings wherein the showings are for the purposes of illustrating preferred embodiments of the invention only and not for purposes of limiting same, FIG. 1 shows an electric toothbrush A according to the present invention. The electric toothbrush can be used for personal hygiene such as brushing one's teeth and gums.

As shown in FIG. 1, the electric toothbrush includes an elongated body portion 10 comprised of a first member 12 detachably connected to a second member 14 at edge line 15. The first member 12 includes a head 16. The second member 14 includes a handle 18.

The head 16 has a traditional larger brush head shape than most known electric toothbrushes which permits the user to brush his teeth in the typical manner of an up and down fashion. As shown on FIG. 2, the length of the head 16, dimension "X", can range from about 0.75 inches to about 1.75 inches. The thickness of the brush head, dimension "Y", can range from about 0.25 inches to about 0.50 inches.

Figure 3:
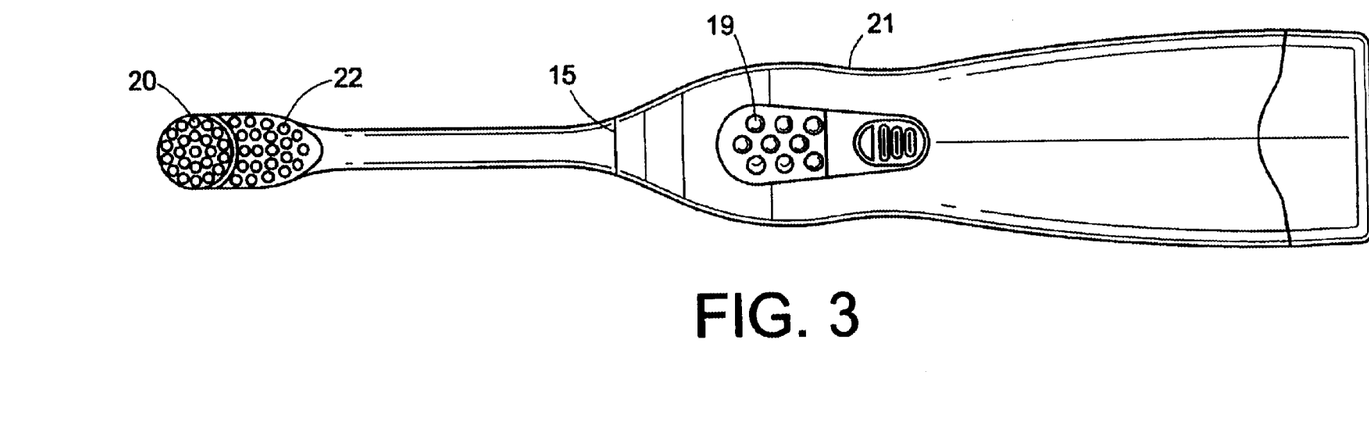
FIG. 3 is a bottom elevational view of the electric toothbrush.

If desired, depressions or grip areas 19 and 21 can be molded into the handle 18 as shown in FIGS. 1 and 3. The depressions and grip areas 19, 21 are used to support a user's thumb and forefinger or other fingers to make using the electric toothbrush easier and more comfortable.

Figure 2:
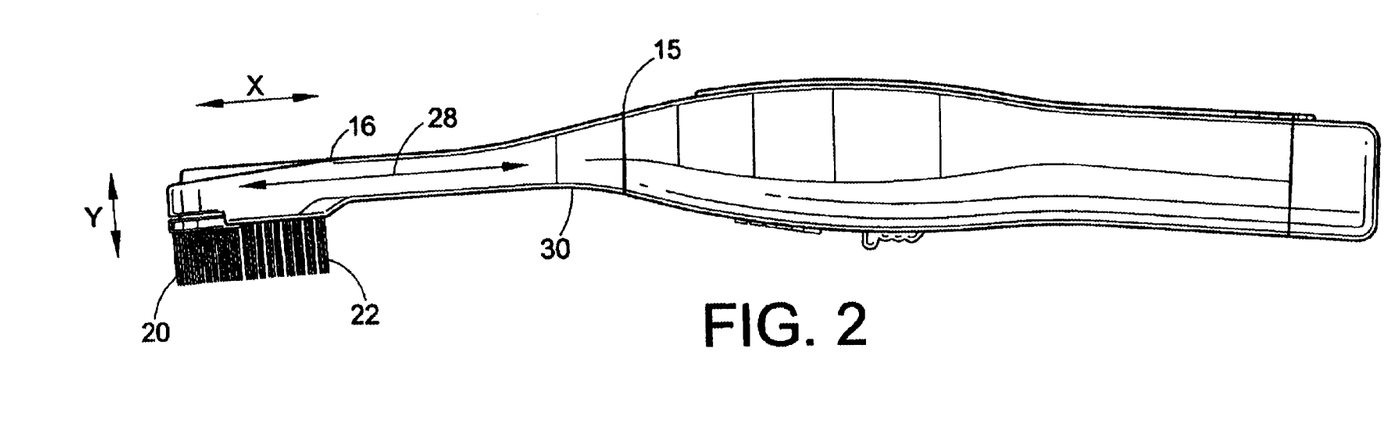
FIG. 2 is a side elevational view of the electric toothbrush of FIG. 1.

Referring now to FIGS. 2 and 3, the head 16 further includes a moving portion or brush head 20 and a static portion or brush head 22. The moving portion 20 includes stiff bristles. The static portion 22 includes soft bristles. The stiff bristles are slightly recessed with respect to the soft bristles. The moving portion 20 rotates about an axis approximately normal to a longitudinal axis 28 of the brush head 16. The stiff bristles aid in the deep cleaning and plaque removal process, while the stationary soft bristles are softer so as to not damage the gums. The length of the bristles can range from about 0.25 inches to about 0.75 inches.

The elongated body portion 10 further includes an angled shaft 30, located between the head 16 and the handle 18. The angled shaft 30 is in line with the longitudinal axis 28 of the head 16. The angle is well known for its ergonomic benefit in permitting easier access into the back recesses of the mouth while still contacting teeth surfaces.

Figure 4A:
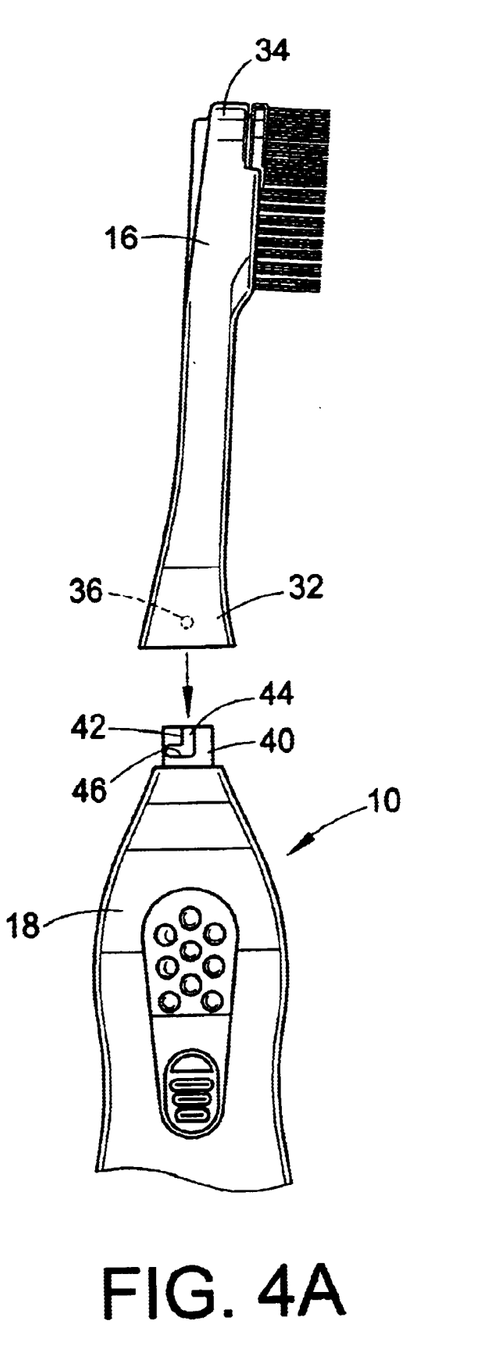
FIGS. 4A and 4B are side elevational views illustrating installation of a first member onto a second member of an elongated shaft of the electric toothbrush of FIG. 1.
Figure 4B:
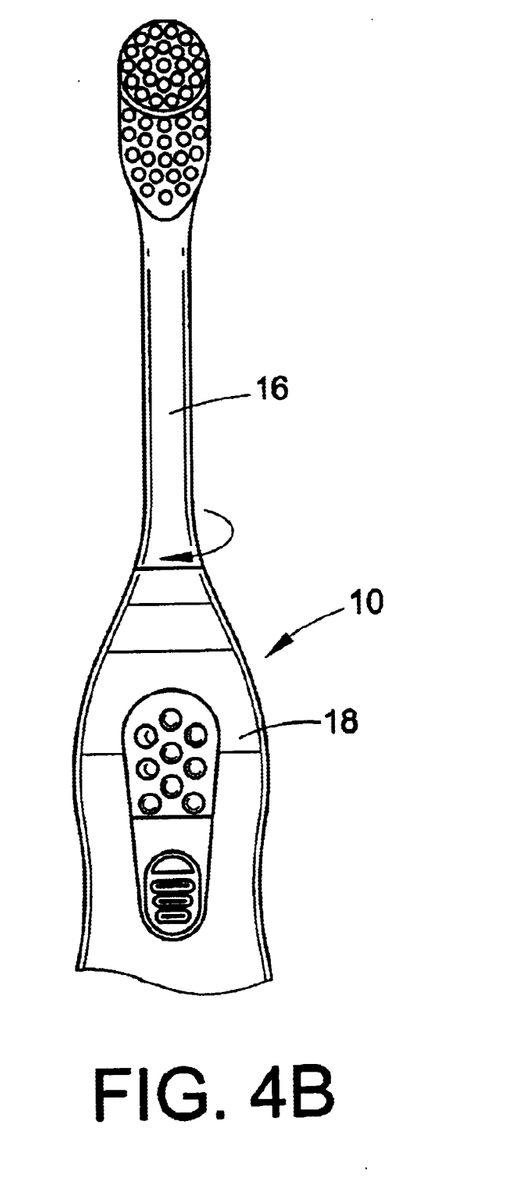

Referring now to FIGS. 4A and 4B, the head 16 contains a first end portion 32 that can connect to the handle 18 and a second end portion 34 where the bristles are attached. The head 16 contains two small pins or projections 36 [in phantom] located inside the head in the end portion 32. The small projections are dimensioned to fit into L-shaped slots 42 found on a mating end portion 40 of the handle 18 of the elongated body 10. The first end 40 of the handle 18 is circular with an outer diameter that is small enough to fit snugly inside the first end portion 32 of the head 16. The width of the L-shaped slots 42 is slightly wider than the width of the small projections to enable the L-shaped slots to receive the small projections. The depth of the L-shaped slots is substantially equal to the height of the small projections so that the L-shaped slots can receive the small projections.

To connect the head 16 to the handle 18, the user aligns the small projections with a top surface 44 of the L-shaped slots. The user pushes or presses the head 16 down so that the small projections contact a bottom surface 46 of the L-shaped slots 42. When the small projections have contacted the bottom surface 46 of the L-shaped slots, the user then turns the head 16 approximately 90 degrees with respect to the handle 16 locking the head into place, as seen in FIG. 4B A top surface of each of the projections becomes locked under a top surface of each of the L-shaped slots 42. The user thus exerts a press-and-twist action on the cooperating pins and guide slots to put the head into a fully attached disposition on the handle and realize a locking engagement between the two.

Figure 5:
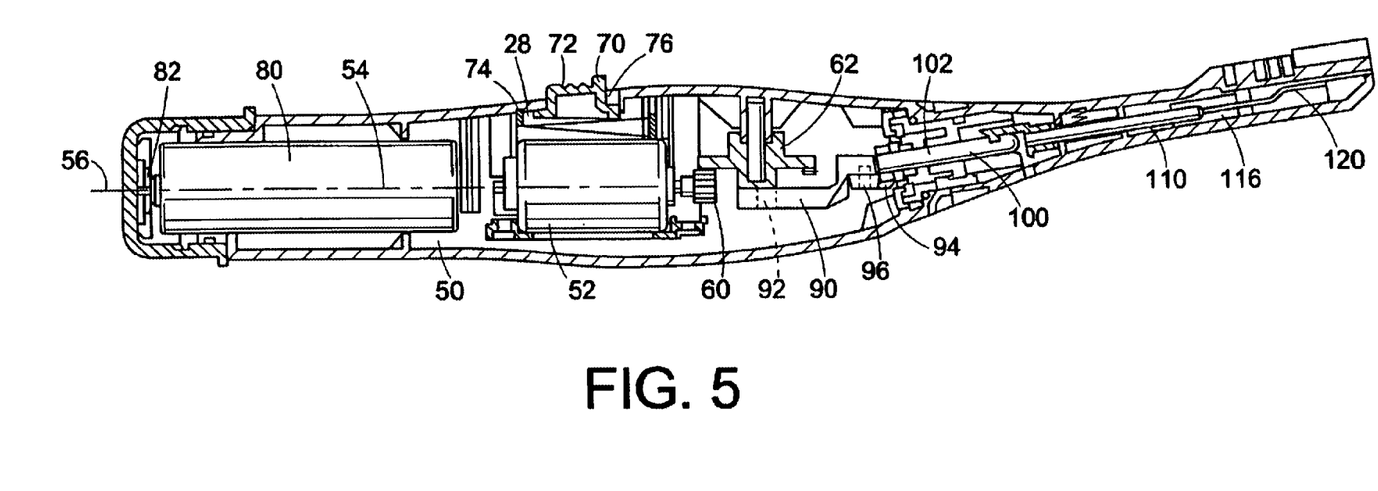
FIG. 5 is a side elevational view in cross section of the electric toothbrush of FIG. 1.
Figure 6:
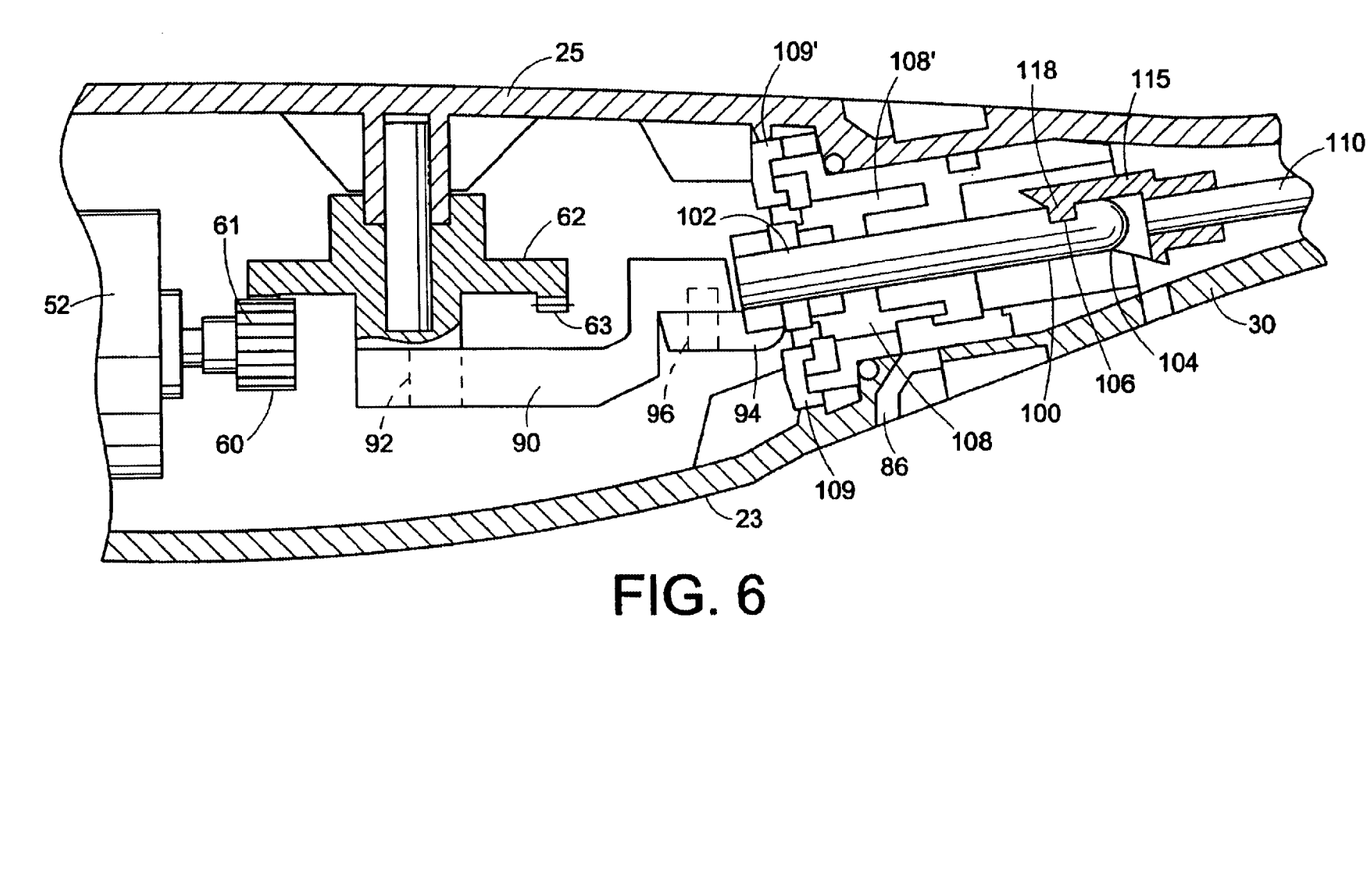
FIG. 6 is an enlarged perspective view of the motor and gear assembly of the electric toothbrush of FIG. 1.

Referring to FIGS. 5 and 6, the elongated body portion 10 further includes a hollow portion 50 that houses a motor 52. The motor 52 has a longitudinal axis 54 in line with a longitudinal axis 56 of the elongated body portion 10.

The embodiment further includes a first gear 60 which is operatively connected to and powered by the motor 52. The first gear 60 rotates about the longitudinal axis 56. A second, crown gear 62 is operatively connected to the first gear 60. The second gear 62 rotates about an axis approximately normal to the longitudinal axis 56 of gear 60. Teeth 61 of the first gear 60 mesh with teeth 63 of the second gear 62, thus causing second gear 62 to rotate when first gear 60 rotates.

A switch 70 is provided to control operation of the electric toothbrush and is operatively connected to the motor 52. The switch 70 includes a molded actuator button 72 and a metal contact 74. The switch 70 is manually depressed by pressing a molded actuator button 72 down, which then presses against a metal contact 74, completing the circuit and providing momentary operation of the toothbrush. The switch 70 also allows continuous operation through a ramp design, sliding the button 72 forward toward the head 16 to provide for continuous operation. Moving the button 72 forward through a slot 76, combined with a molded in ramp 78 in the metal contact 74, causes the button 72 to move downward, pressing against the metal contact 74 and completing the circuit. The toothbrush then continuously operates until the button 72 is slid back into an off position toward the handle 18 and the button 72 disengages the metal contact 74.

By combining these two functions in one switch 70, the toothbrush can be packaged in packaging where the consumer can depress the button 72 through the packaging and see its operation while still inside the packing, and then be able to operate it continuously once out of the package. It should be noted that other sizes and shapes of buttons may be used.

A battery 80 is provided within the hollow portion 50 of the elongated body portion 10. A battery terminal or contact 82 is provided for the battery 80. AA batteries can be used as is illustrated in FIG. 5.

Vent holes 86 are provided in the upper housing 23. The vent holes 86 are located in the angled shaft 30 area of the elongated body portion 10. The vent holes 86 allow any water or saliva that may have entered into the brush to exit before reaching the motor and gear assembly.

Referring to FIG. 6, a first linkage or swivel arm 90 is pivotably connected to the second gear 62 via a pin 92 or other fastening device. A second linkage or swivel arm 94 is pivotably connected to the first swivel arm 90 via a pin 96 or other fastening device. A first shaft 100 is fixedly secured at a shaft first end 102 to the second swivel arm 94. The shaft 100 is housed within the angled shaft 30. The shaft 100 can attach at a shaft second end 104 to an extension 115. The extension 115 connects first shaft 100 to a second shaft 110. Extension 115 has a protrusion or tab 118 which engages a corresponding notch 106 within the second end 104 of shaft 100. The extension 115 is further connected to second shaft 110.

Front rubber sleeve locators 108, 108' and rear rubber sleeve locators 109, 109' align the first shaft 100. The front rubber sleeve locators 108, 108' are located near the first shaft's first end 102. The front rubber sleeve locators are between the first shaft 100 and the upper and lower housings 23, 25. The rear rubber sleeve locators 109, 109' are also located near the first end 102 of the first shaft 100. The rear rubber sleeve locators 109, 109' are closer to the head 16 of the brush than are the front rubber sleeve locators 108, 108'.

The first shaft 100 is generally parallel with the longitudinal axis 28 of the head 16 as seen in FIG. 5. A second adapter 116 connects the second shaft 110 to a third swivel arm 120. The third swivel arm 120 is pivotably connected to a disk of the moving bristle portion 20 by a pin or other fastening device. The disk is housed within the head 16.

As the first gear 60 rotates, the second gear 62 is rotated, thus moving the first swivel arm 90 in a back and forth circular fashion about the second gear 62 and along the longitudinal axis 56. The first swivel arm 90 also can pivot about the pin 92. The first swivel arm 90 retains its orientation of approximately parallel to the longitudinal axis 56 of the elongated body portion 10 during movement. The second swivel arm 94 pivots with respect to its pin connection 96 with the first swivel arm 90 thus allowing the first shaft 100 to oscillate in a back and forth manner toward and away from the brush head with minimal lateral motion.

Figure 7A:
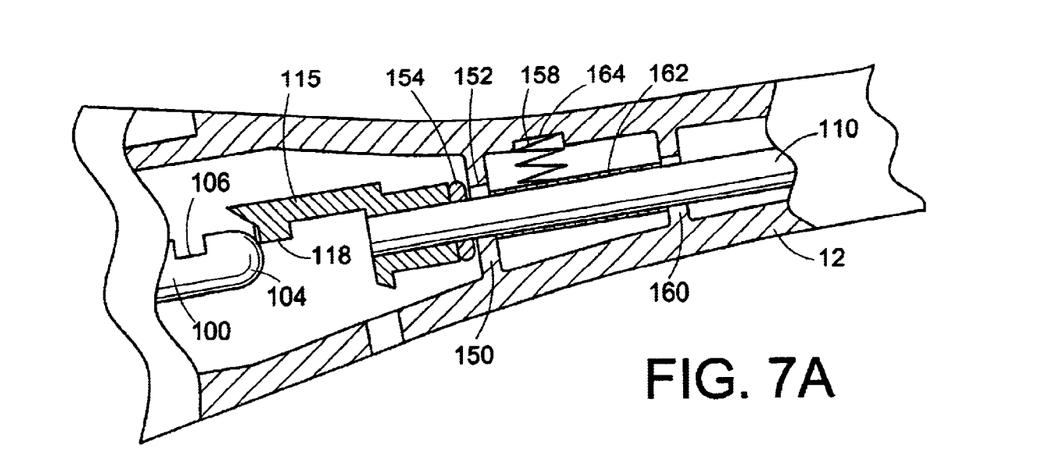
FIG. 7A is a side cross-sectional view of a first and a second shaft within a first portion of the toothbrush prior to engagement.
Figure 7B:
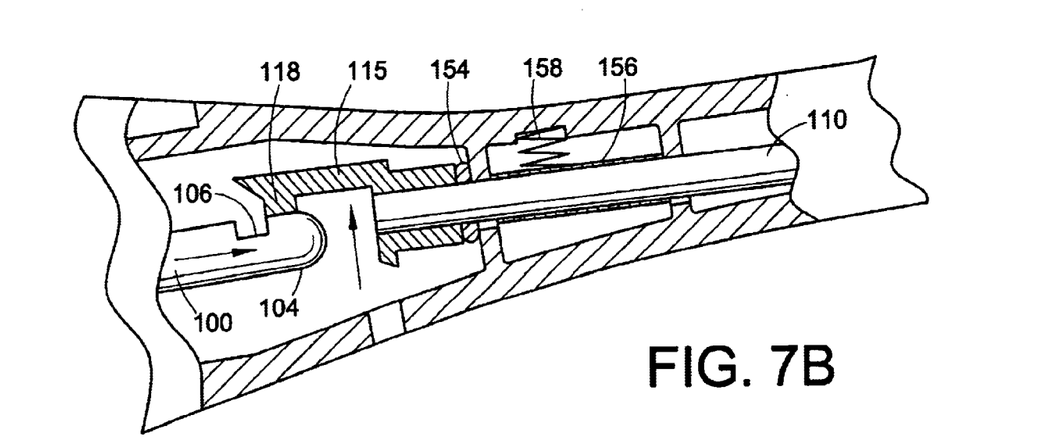
FIG. 7B is a side cross-sectional view of the first and second shafts of FIG. 7A as a peg and notch on the shafts begin to engage.
Figure 7C:
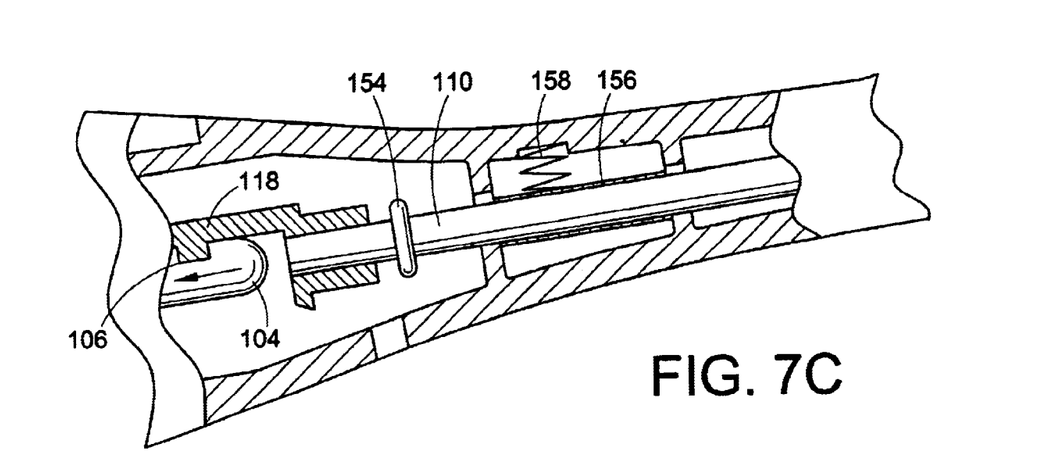
FIG. 7C is a side cross-sectional view of the first and second shafts of FIG. 7A with the peg and notch in full engagement.

During operation, the third swivel arm 120 moves back and forth along the longitudinal axis 28 along with the second shaft 110. The third swivel arm 120 can also pivot or move slightly laterally in a direction perpendicular to the longitudinal axis 28 for an angular movement accommodating the locking engagement between the head and handle, as will be better explained with reference to FIG. 7.

Referring to FIGS. 7A, 7B, 7C, the first member 12 of the elongated body portion is hollow. A wall 150 containing a hole 152 is disposed inside the first member 12 located generally in the middle of the first member 12. The hole 152 is generally round in shape with its center being located along the longitudinal axis 28. The hole 152 is large enough so that the second shaft 110 may move freely inside of it without contacting the wall 150. The hole 152 is also large enough so that the shaft 110 can deflect through an angular movement enough to allow the second end 104 of first shaft 100 to move over the peg 118 and be received in the notch 106.

A ring 154 is disposed between the wall 150 and the adapter 115 and surrounds the second shaft 110. The ring can be fabricated from rubber or another flexible material. The inner circumference of the ring 154 is large enough that the shaft 110 will move freely inside the ring. The ring 154 is large enough that it will not go through the hole 152 in the wall 150.

A bushing 156 surrounds a portion of the shaft 110. The bushing 156 can be made from a thermoplastic material. The bushing 156 is disposed between the wall 150 and a second wall 160 which has an opening 162 large enough for the shaft 110 to pass through. The inner diameter of the bushing is large enough to allow the shaft 110 to move freely inside of the bushing. A biasing member or spring 158 connects the bushing 156 to an inner wall 164 of the first member of the elongated body 12 and biases the shaft 110 away from the inner wall 164.

Referring to FIGS. 7B and 7C, to connect the second shaft 110 to first shaft 100, shaft 100 moves along the longitudinal axis 28 toward shaft 110. The first end 104 of shaft 100 contacts the adapter 115. The adapter 115 moves along the longitudinal axis 28 towards the head 16 and contacts the ring 154. The ring 154 in turn contacts the wall 150 and thus prevents further longitudinal movement of shaft 110. The shaft 110 then deflects away from the longitudinal axis 28 toward and against the biasing member 158 allowing the first end 104 on shaft 100 to ride over peg 118 and allow the peg to engage the notch 106. After peg 118 engages the notch 106, the biasing member 158 will bias the shaft 110 back toward the longitudinal axis 28 thus connecting the shaft 100 to shaft 110.

Figure 8A:
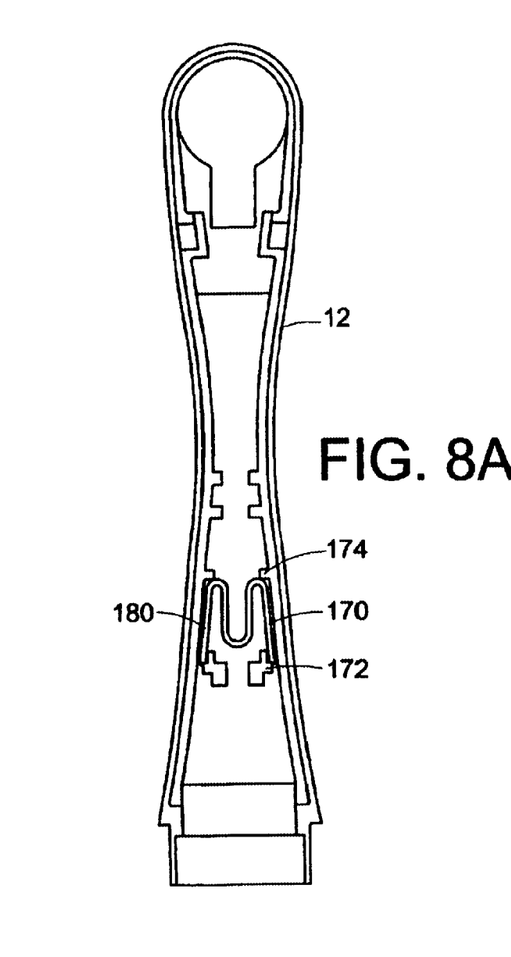
FIG. 8A is a cross-sectional view of the head portion comprising an alternative spring member construction of a flat spring.
Figure 8B:
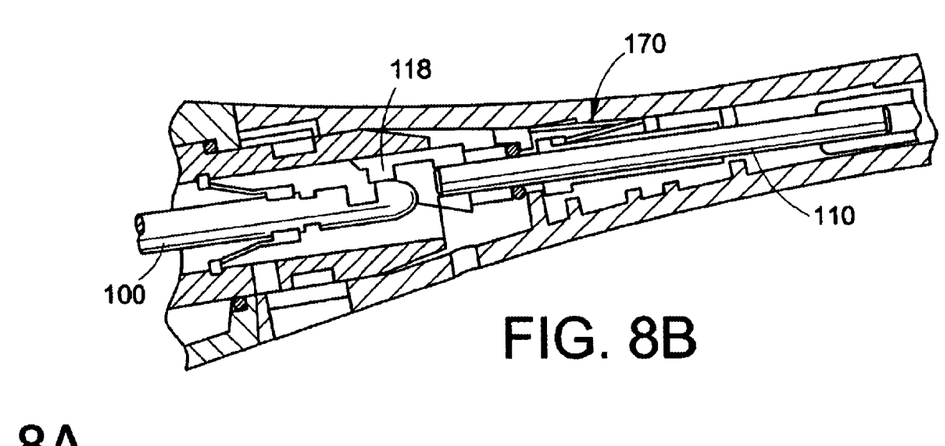
FIGS. 8B and 8C show the embodiment of FIG. 8A where the spring is compressed and relaxed, respectively.
Figure 8C:
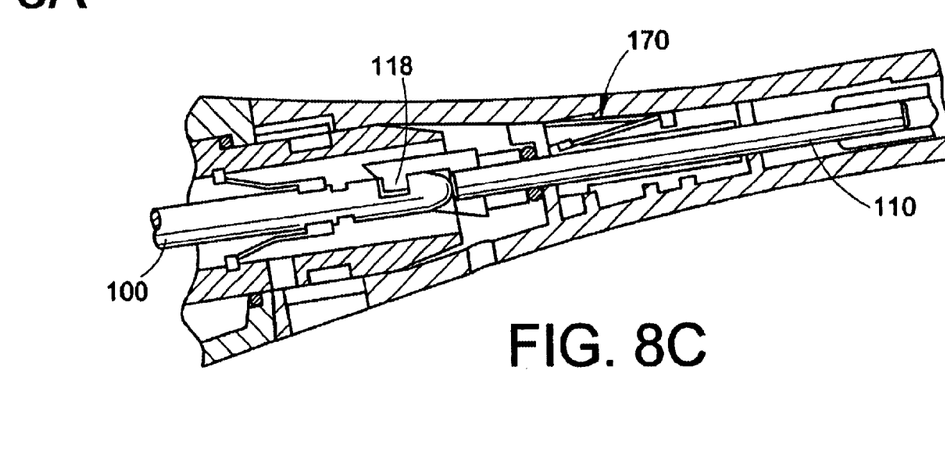

With reference to FIGS. 8A–8C, an alternative embodiment of the replaceable head assembly is shown wherein the biasing spring member comprises a flat, M-shaped spring 170 for biasing the second shaft 110 towards the first drive shaft 100. The spring 170 is located within the replaceable head 12 by integrally molded guide members 172, 174. The central portion 180 of the spring physically engages the side wall of the shaft 110 so that as the end portion 118 cams over the end portion of the first drive shaft 100, the biasing spring 170 will continuously urge the peg 118 to engage the notch 106 as in the embodiment of FIG. 7.

Figure 9A:
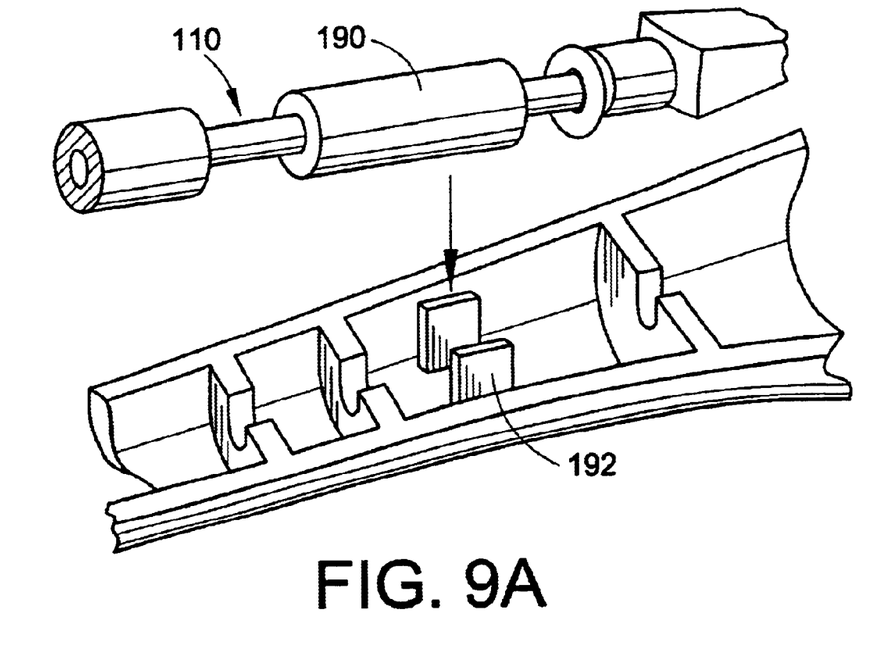
FIG. 9A is an exploded assembly view of a portion of the toothbrush showing yet another spring embodiment; and, FIGS. 9B and 9C are cross-sectional views that show the embodiment of FIG. 9A where the spring is relaxed and compressed, respectively.
Figure 9B:
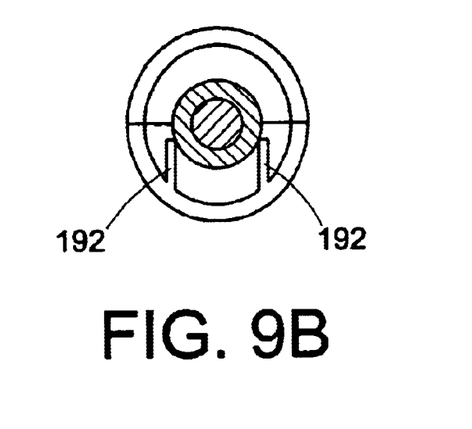
Figure 9C:
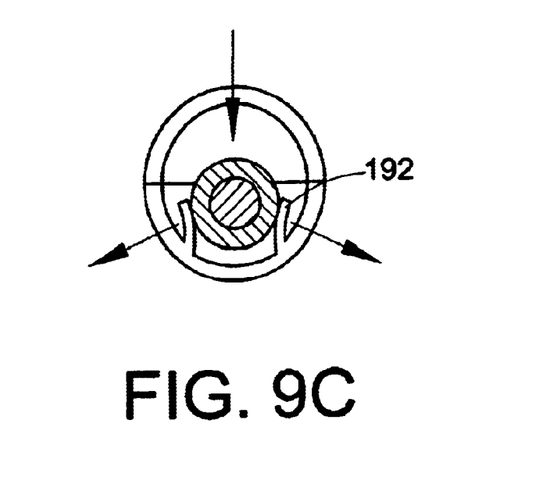

With reference to FIGS. 9A–9C, yet another embodiment is illustrated wherein the drive shaft 110 includes a circumferential bushing 190 sized for causing a spring deflection in spring ribs 192 as the drive shaft is cammingly urged towards the ribs 192 when peg 118 rides over the end 104 of shaft 100 towards notch 106. The spring ribs 192 are integrally molded into the side wall of the replaceable head housing of a deflectable plastic material and to cause the deflection as can be better seen in FIG. 9C when bushing 190 is pressed down toward the side wall of the housing. The ribs or prongs 192 thus extend radially internally toward the center of the housing to exert a spring-like pressure towards the drive shaft in the manner of the springs 154, 170 of the prior discussed embodiments.

The invention is preferably marketed in a kit form with a single handle member 18 and a plurality of replaceable heads 16. The heads can thus be replacements or individually assigned to different members of a family. Color distinction is thus often a part of the different heads in a kit. Although the handle is discussed as preferably battery powered, of course, the invention also includes other well known power supplies such as corded for outlet connection or rechargeable batteries and an associated brush holder/charger (not shown). The kit includes the possibility of housing one or more batteries with the replaceable head(s).

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. An electric toothbrush comprising:
an elongated body including a handle housing a motor, and a head having moving bristles, wherein the head is detachably connected to the handle and wherein the moving bristles are operatively connected to the motor; and,
a shaft assembly for the operatively connecting of the bristles and motor comprising first and second shafts respectively associated with the motor and bristles, wherein the first shaft includes a notch at an end portion and the second shaft includes a tab sized for reception in the notch, and wherein the second shaft is biased for selective angular movement towards the first shaft by a spring member for locking engagement between the tab and the notch upon operative attachment of the head to the handle.

2. The toothbrush as defined in claim 1 wherein the second shaft includes a shaft extension depending from an end portion of the second shaft, the shaft extension including the tab.

3. The toothbrush as defined in claim 2 wherein the notch is disposed in the first shaft and the tab is disposed in the extension for the locking engagement upon selective alignment of the head and the handle in a predetermined attached position.

4. The toothbrush as defined in claim 3 wherein the handle includes a guide slot at an end portion of the handle for receiving a mating projection from the head whereby the cooperative reception between the mating projection and the slot aligns the head and the handle in the predetermined attached position.

5. The toothbrush as defined in claim 1 wherein the head includes an inner wall forming an aperture loosely spaced about the second shaft for accommodating the selective angular movement, the wall being disposed intermediate the tab and the spring.

6. The toothbrush as defined in claim 1 wherein the head includes a swivel arm depending from the second shaft, the selective angular movement of the second shaft comprising a pivot of the second shaft from the swivel arm.

7. The toothbrush as defined in claim 1 wherein the spring member comprises a flat spring.

8. The toothbrush as defined in claim 1 wherein the spring member comprises rib springs.

9. The toothbrush as defined in claim 8 wherein the second shaft includes a bushing sized for deflection of the rib springs.

10. The toothbrush as defined in claim 1 wherein the toothbrush comprises a kit assembly including a plurality of heads and a battery for the motor.

11. An electric toothbrush with a replaceable head, wherein bristle movement in the head is effected by a reciprocating head shaft powered by a motor in a handle attached to the replaceable head, the toothbrush comprising:
mating head and handle portions including a cooperating pin and guide slot for defining a fully attached disposition of the head on the handle by a press-and-twist operator action; and,
the head shaft disposed for locking engagement with a handle shaft operatively associated with the motor for communicating a desired reciprocating movement to the head shaft, wherein the head shaft is biased into the locking engagement by a spring member buttressed by a wall of the replaceable head when the head is in the fully attached disposition to engage the head shaft and urge the head shaft into a desired position relative to the handle shaft.

12. The toothbrush as claimed in claim 11 wherein the head and handle shafts include a cooperating notch and tab assembly defining the locking engagement in the fully attached disposition.

13. The toothbrush as claimed in claim 12 wherein the notch and tab assembly is configured to avoid the locking engagement at a relative rotational position between the head and handle other than the fully attached disposition.

14. The toothbrush as claimed in claim 12 wherein the head shaft is biased by the spring member for angular movement into and out of the locking engagement in accordance with a relative rotational disposition of the head and the handle effected by the press-and-twist operator action.

15. The toothbrush as defined in claim 12 wherein the second shaft includes a bushing sized for deflection of the rib springs.

16. The toothbrush as defined in claim 11 wherein the spring member comprises a flat spring.

17. The toothbrush as defined in claim 11 wherein the spring member comprises rib springs.

18. The toothbrush as defined in claim 11 wherein the toothbrush comprises a kit assembly including a plurality of heads and a battery for the motor.

19. A replaceable head for reception onto an electric toothbrush handle, the toothbrush handle including a motor and motor shaft, the head comprising moving bristles and a drive shaft for communicating movement from the motor to the moving bristles; by an engagement between the motor shaft and the drive shaft and wherein the drive shaft is biased into a selected locking engagement of the motor shaft by a spring member that is buttressed against a side wall of a housing comprising the head and which is disposed to contact and urge the drive shaft into the locking engagement.

20. The head as defined in claim 19 wherein the spring member comprises a flat spring.

21. The head as defined in claim 19 wherein the spring member comprises rib springs.

22. The head as defined in claim 21 wherein the rib springs are integrally molded with and depend from a side wall of the head.

* * * * *